US005289858A

United States Patent [19]

Grabenkort

[11] Patent Number: 5,289,858

[45] Date of Patent: Mar. 1, 1994

[54] SYSTEM FOR ACCOMMODATING WITHDRAWAL OF LIQUID FROM A BULK SUPPLY

[75] Inventor: Richard W. Grabenkort, Barrington, Ill.

[73] Assignee: Abbott Laboratories, Abbott Park, Ill.

[21] Appl. No.: 809,592

[22] Filed: Dec. 18, 1991

[51] Int. Cl.⁵ .......................... A61M 5/00; B65D 3/04

[52] U.S. Cl. .......................... 141/97; 141/114; 141/98; 141/329; 141/86; 141/390; 604/82; 604/199; 604/411; 604/403; 604/415

[58] Field of Search .......................... 141/97, 114, 86, 88, 141/329, 330, 98, 390; 604/199, 82, 403–415; 206/219, 570; 383/4

[56] References Cited

U.S. PATENT DOCUMENTS

| | | | |
|---|---|---|---|
| 4,564,054 | 1/1986 | Gustavsson | 141/329 |
| 4,600,040 | 7/1986 | Näslund | 141/329 X |
| 4,619,651 | 10/1986 | Kopfer et al. | 604/415 |
| 4,671,331 | 6/1987 | Pruden | 141/98 |
| 4,673,404 | 6/1987 | Gustavsson | 604/411 |
| 4,834,149 | 5/1989 | Fournier et al. | 604/199 X |
| 4,845,781 | 7/1989 | Strickland et al. | 383/4 X |
| 4,909,290 | 3/1990 | Coccia | 141/329 |
| 5,064,945 | 11/1991 | Ryan et al. | 604/198 |
| 5,088,996 | 2/1992 | Kopfer et al. | 604/415 |

*Primary Examiner*—Ernest G. Cusick

*Attorney, Agent, or Firm*—A. Nicholas Trausch

[57] ABSTRACT

A protection system is provided for the transfer of toxic liquid from a bulk container through a first conduit to a connector for a delivery device such as a dosage syringe. A second conduit connects the connector to a waste receptacle. The first and second conduits penetrate the closed end of a flexible barrier bag. The bag is initially retracted from the bulk container to allow manipulation of the bulk container. The bag is subsequently extended over and sealed around the bulk container and waste receptacle to protect the health care provider during liquid transfer to the deliver device.

12 Claims, 4 Drawing Sheets

SYSTEM FOR ACCOMMODATING WITHDRAWAL OF LIQUID FROM A BULK SUPPLY

TECHNICAL FIELD

The present invention relates to a fluid transfer system for accommodating the withdrawal of liquid from a bulk supply for use in medical procedures. The present invention is particularly well-suited for use with bulk reconstituted, toxic drugs, such as chemotherapeutic drugs.

BACKGROUND OF THE INVENTION AND TECHNICAL PROBLEMS POSED BY THE PRIOR ART

Various medical procedures require the transfer of fluid from one fluid-containment system or fluid-conducting system to another fluid-containment system or fluid-conducting system. Typically, one of the two systems includes a container for a bulk supply of liquid, such as a bulk supply of a reconstituted, liquid, chemotherapeutic drug. The other system, which can be as simple as a syringe, may be connected to the first system for only a short period of time, or intermittently, to facilitate the withdrawal of a desired amount or dose of the liquid for administration or transmission to a patient.

In those medical applications where the first system includes a container for a bulk supply of a toxic liquid, it is desirable, if not necessary, to prevent inadvertent exposure of personnel to the toxic liquid. For example, a hospital pharmacy may prepare highly toxic, chemotherapeutic drugs for use in treating cancer patients. Typically, a vial of a highly concentrated, toxic drug is received from the pharmaceutical supplier by the hospital pharmacy, and the hospital personnel then admix the concentrated drug with a suitable diluent to provide a bulk reconstituted supply having a reduced concentration or effective dose per unit volume that permits the administration of a prescribed amount or volume directly to the patient.

The preparation of the bulk reconstituted, liquid drug is typically carried out in a protective environment, such as in a laminar flow hood which is specially designed to maintain a negative pressure within the hood so as to prevent the escape of toxic vapors.

The bulk reconstituted, liquid drug is usually stored in a suitable container which may be a flexible, thermoplastic, sealed bag. A suitable discharge structure, dispensing structure, or fitment is typically provided on the bulk container to accommodate withdrawal of a desired amount of the liquid from the container. It is, of course, desirable to ensure that the means for withdrawing a prescribed amount of the toxic liquid drug will not result in spills or leaks from the bulk container.

Accordingly, it would be advantageous to provide a barrier system which could be employed with a container of a bulk supply of a toxic drug and which would function to contain a leak or leaks of the liquid drug from the container, or from associated connections thereto, so as to prevent exposure of personnel to the drug.

It would also be desirable to provide such a barrier system with means for accommodating its disposition in association with, or its connection to, the bulk supply container in a manner that can be relatively easily and quickly effected.

It would also be beneficial if such a barrier system could be provided with a structure that would accommodate movement or transport of the bulk supply from one location to another while still maintaining the efficacy of the barrier system against leakage.

Further, it would be desirable to provide such a barrier system with means for accommodating withdrawal of the bulk reconstituted, liquid drug by means of a suitable, conventional syringe, especially a syringe having a luer fitment.

It would also be advantageous for such a barrier system to function to prevent inadvertent injection of the liquid drug, or other material, back into the bulk container so as to reduce the probability of contamination of the bulk supply.

In addition, it would be beneficial if the barrier system could accommodate the use of a syringe to withdraw the liquid drug from the bulk supply and to pump a desired volume of the liquid drug into a selected conduit for administration to a patient or for delivery to another container or containment system.

When a bulk container of liquid is employed for supplying small quantities or doses of the liquid drug via withdrawal by a syringe, it would be desirable to provide means for accommodating the aspiration or discharge from the syringe of an excess amount of the liquid, or of a portion of the liquid in which an air bubble is entrained, that may have been drawn into the syringe. It would be desirable to provide such a capability regardless of whether or not the bulk supply of liquid is toxic.

Accordingly, it would be desirable to provide a suitable receiving compartment or receptacle for excess liquid and/or for a mixture of liquid and air, in conjunction with a syringe-operated transfer or withdrawal system operable on a bulk supply. It would be beneficial if such a receptacle could be provided as a unitary or integral part of the withdrawal system and could also be adapted for use with a barrier system that prevents exposure of personnel to leakage.

Further, in view of the dangers associated with toxic drugs, contamination, and infection, it would be desirable to provide a barrier system and/or receptacle system which would facilitate its use as a disposable item. To this end, such a system or systems should be relatively inexpensive. Accordingly, such systems should incorporate an improved component design that accommodates relatively simple manufacturing processes and assembly processes to keep the total cost as low as possible.

The systems should also function to effectively seal at connection points or attachment points to prevent leakage of fluids and to prevent ingress of airborne or liquid-carried contaminants.

Additionally, the systems should preferably function effectively with a variety of fluids throughout a range of fluid pressures.

Advantageously, the systems should have a suitably long shelf life and active use life. Further, such systems should preferably be adaptable to function effectively after repeated connections to a syringe.

SUMMARY OF THE INVENTION

The present invention provides a novel fluid transfer system for accommodating the withdrawal of liquid form a bulk supply. In the preferred form, the invention permits a bulk supply of hazardous liquid to be prepared, such as by the admixing of a highly concentrated, toxic drug with a diluent, while preventing or minimizing exposure of personnel to the hazardous liquid. This is facilitated by the use of a novel barrier system which is impervious to the liquid.

The barrier system of the present invention functions effectively to protect personnel from spills or leaks of a hazardous liquid during withdrawal of the liquid from a bulk supply and/or during preparation of the bulk supply. The barrier system conveniently permits manual operations to be performed on various components, such as a small container of a highly concentrated, toxic drug and a larger container of a diluent liquid.

The barrier system accommodates the movement or transport of a bulk supply of liquid from one location to another while maintaining the efficacy of the barrier system protection against leakage. Further, the barrier system accommodates the convenient withdrawal of liquid from the bulk supply by means of conventional components, such as a suitable syringe.

Another aspect of the invention, which can provide operational advantages with or without a protective barrier system of the type referred to above, relates to a system for accommodating the collection of unwanted or excess liquid that has been inadvertently withdrawn or otherwise withdrawn from a bulk supply. In particular, when a syringe is used for withdrawing liquid from a bulk supply container, the system permits a portion of the liquid in the syringe, which may be an excess amount, or which may contain an air bubble, to be discharged from the syringe to a novel waste receptacle.

The liquid transfer and waste-receiving system is adapted to be conveniently used in conjunction with a bulk supply of liquid. The waste-receiving system is especially well-suited for use in conjunction with, and as a integral part of, the above-discussed personnel protection barrier system.

Both systems, whether provided separately or as an integral combination system, can incorporate improved component designs which accommodate relatively simple manufacturing processes and assembly processes so as to keep the total cost as low as possible. The systems can function effectively with a variety of fluids through a range of fluid pressures. The systems accommodate designs that provide a suitably long shelf life and active use life.

In one preferred form of the invention, a protection system is provided for a container from which a hazardous liquid can be removed. The system includes conduit means for being connected to, and extending from, the container to define a flow path for the liquid from the container to a discharge location exterior of the container. A flexible barrier, which is impervious to the liquid, is penetrated by, and sealed to, the conduit means. The flexible barrier accommodates at least two arrangements: (1) an initial arrangement in a retracted orientation permitting access to, and manipulation of, at least a portion of the conduit means and container; and (2) a subsequent arrangement in an extended orientation enveloping a portion of the conduit means and the connected container.

The liquid transfer or withdrawal system, which may operate separately from, and independently of, the above-described barrier system, accommodates the withdrawal of liquid from a container with a syringe. The withdrawal system includes a first conduit means for being connected at one end to, and for extending from, the container. The first conduit means is connected at another end to the syringe to define a flow path for the liquid between the container and the syringe.

A second conduit means is provided for defining a flow path for the liquid from a first end connected to, and in fluid communication with, the first conduit means. The receptacle is connected to the second end of the second conduit means and is in fluid communication therewith. A first one way, non-return valve is provided in the first conduit means in the flow path between the container and the second conduit means to prevent flow into the container. A second one-way, non-return valve is provided in the second conduit means to prevent flow out of the receptacle to the first conduit means.

Numerous other advantages and features of the present invention will become readily apparent from the following detailed description of the invention, from the claims, and from the accompanying drawings.

BRIEF DESCRIPTION OF THE DRAWING

In the accompanying drawings that form part of the specification, and in which like numerals are employed to designate like parts throughout the same.

DESCRIPTION OF THE PREFERRED EMBODIMENTS

Figure 1:
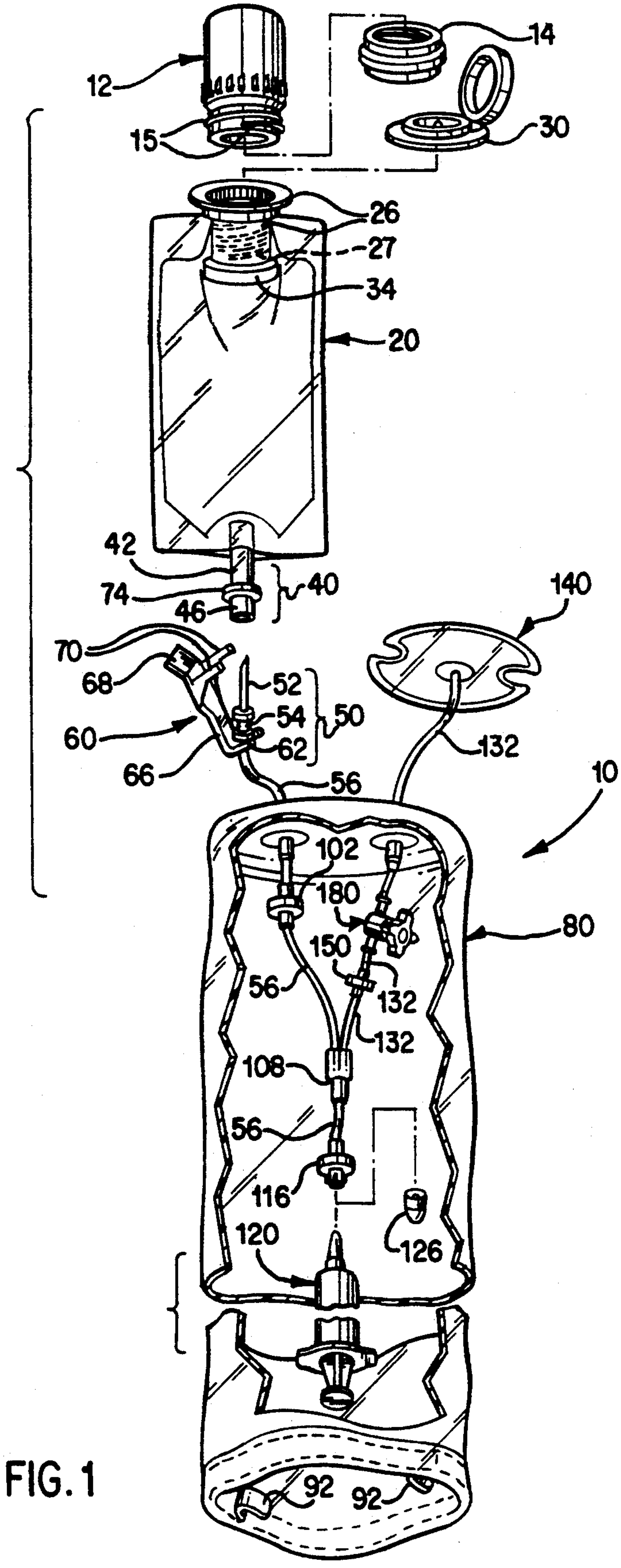
FIG. 1 is a partially exploded, perspective view of the components of a preferred form of the present invention shown in a first orientation in conjunction with a drug vial and diluent bag, and a portion of a component of the invention has been broken away to better illustrate interior details.

The present invention provides a novel transfer system for accommodating the withdrawal of liquid from a bulk supply. The invention is particularly well-suited for use with bulk reconstituted, toxic drugs, such as chemotherapeutic drugs.

One aspect of the invention relates to a novel barrier system for protecting personnel from leaks or spills of a hazardous liquid that is stored in a container from which the liquid can be removed. Another aspect of the invention, which may be included as an integral part of, or which may be entirely independent of, the barrier system, provides a unique liquid transfer system for accommodating the use of a syringe to draw liquid from a container. The liquid transfer system provides a novel receptacle for receiving a portion of the withdrawn liquid which may be an excess amount and/or which may contain an entrained air bubble.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the system components of this invention are described in an arbitrarily selected operating position, and terms such as upper, lower, horizontal, etc., are used with reference to this position. It will be understood, however, that the components of this invention may be manufactured, stored, transported, and sold in a partially or fully disassembled state, as well as in orientations other than that described.

The FIGURES illustrating embodiments of the components show structural details that will be recognized by one skilled in the art. However, the detailed descriptions of all such details are not necessary to an understanding of the invention, and accordingly, are not herein presented.

The system components of this invention may typically be used with certain conventional components the details of which, although not fully illustrated or described, will be apparent to those having skill in the art and an understanding of the necessary functions of such components.

The first embodiment of the present invention is illustrated in FIGS. 1–5 wherein a transfer system is designated generally by the reference numeral 10. The system 10 may be conveniently employed to accommodate the preparation and use of a bulk reconstituted, toxic drug. A toxic drug is typically provided in a highly concentrated form contained in a small vial 12. The vial 12 typically includes a removable closure 14 which is initially sealingly mounted over the mouth of the container 12 and sealed thereto with a frangible web. The closure 14 can be torn away to permit removal of the closure 14 so as to expose exterior threads 15 on the neck of the vial 12.

The opening or neck of the vial 12 typically contains an internal, removable, resilient, seal plug 23 (not visible in FIG. 1 but shown removed in FIG. 2) The seal plug 23 defines an outwardly opening receiving cavity or recess, and the seal plug 23 prevents the discharge, or removal, of the liquid contents from the vial 12 unless and until the plug 23 is engaged and removed in a certain manner by an appropriate mating structure, such as may be incorporated in a bulk supply container or bag 20 described hereinafter.

A conventional vial 12 is sold in the U.S.A. as part of the Add-Vantage® brand bulk reconstituted, drug system sold in the U.S.A. by Abbott Laboratories, Inc., One Abbott Park Road, Abbott Park, Illinois 60064-3500 U.S.A. The detailed design and specific structure of the vial 12 form no part of the present invention.

The bulk supply container or bag 20 may be of any appropriate design that is suitable for use with the particular liquid to be stored and that is suitable for use with the vial 12 if such a vial 12 is employed.

The bag 20 is preferably fabricated from a conventional, flexible, transparent, thermoplastic material. The bag 20 normally would be furnished to a hospital or other user with a bulk supply of liquid sealed therein. If the bag 20 is to be used for the administration of a toxic drug, the bag 20 may contain a diluent liquid and may be adapted to be connected to the highly concentrated drug vial 12.

To this end, the bag 20 includes a neck 26 defining an opening to the bag interior. The opening is initially occluded with an outer closure 30 that is connected to the neck 26 with a frangible seal. The outer closure 30 can be torn away from the bag neck 26 to permit the vial 12 to be coupled to the neck 26. To this end, the neck 26 may include internal threads 27 for mating with the threads 15 on the neck of the vial 12.

Figure 2:
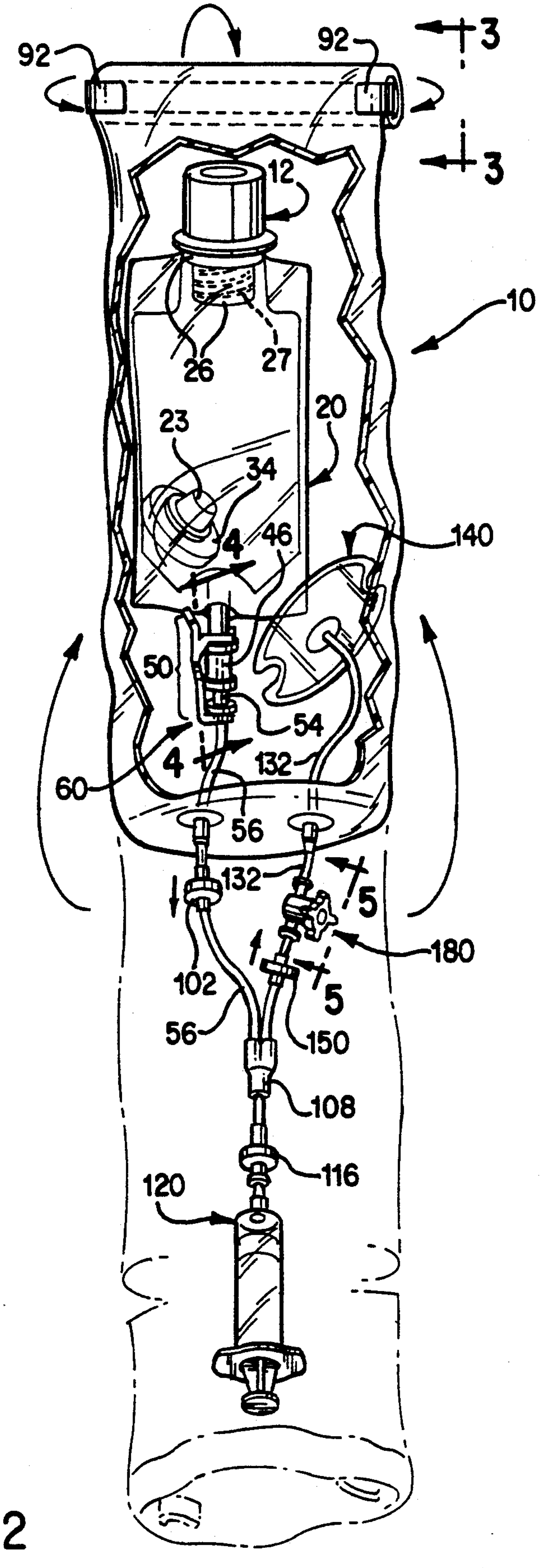
FIG. 2 is a view similar to FIG. 1, but FIG. 2 shows the components after various fluid connections have been made and after the components have been rearranged in a second orientation to provide protection against fluid leakage.

Inside the bag neck 26 there is an inner plug 34 with an upwardly projecting member (not visible) for being received in the recess of the seal plug 23 inside the neck of the vial 12 and for tightly engaging the resilient seal plug 23. As the vial 12 and bag 20 are screwed together, the projecting member is driven into engagement with the vial seal plug 23. Next, the bag plug 34 is manually disengaged from the bottom of the neck 26 by pushing the flexible walls of the bag 20 against the projecting flange of the plug 34 and pulling the plug 34 out of the neck 26. This causes the projecting member of the plug 34 to also pull the engaged seal plug 23 out of the neck of the vial 12. The two, engaged plugs then drop together to the bottom of the bag 20 as illustrated in FIG. 2.

The above-described structure of the bag neck 26 and end closure is a conventional design provided on bags for use with the above-described type of vial 12. Such a bag neck and closure structure is employed with bags furnished with the above-described Add-Vantage® drug administration system sold by Abbott Laboratories, Inc. The detailed design and specific structure of the neck 26, outer closure 30, and inner plug 34 form no part of the present invention. Designs for the connection structure for the bag 20 and vial 12 are also disclosed in the Abbott Laboratories, Inc., U.S. Pat. Nos. 4,614,267, 4,614,515, and 4,757,911.

After the plugs have been dislodged from the necks of the bag 20 and vial 12, the concentrated liquid drug from the vial 12 flows into the bag 20. The flexible bag 20 may then be kneaded or otherwise manipulated to effect a thorough mixing so as to produce a bulk reconstituted drug having a much lower concentration. The lower concentration is determined, of course, by the initial amount of the concentrated drug in the vial 12 and by the initial amount of the diluent in the bag 20.

At the end of the bag 20 opposite the neck 26 there is a discharge structure or dispensing fitment 40 (FIG. 1). The fitment 40 includes a suitable tube 42, such as a rigid, thermoplastic tube which projects from the bottom of the bag 20. The tube 42 extends through the flexible end wall of the bag 20, and the bag wall is sealed around the periphery of the tube 42. This seal may be effected with conventional heat seal techniques, with adhesive, or by other means, the details of which form no part of the present invention.

The tube 42 is in fluid communication with the liquid in the interior of the bag 20. The liquid is prevented from discharging from the tube 42 by a suitable closure or fitment 46 which is preferably in the form of a seal or "reseal" that accommodates penetration by a suitable hollow spike, hollow needle, or cannula. Such a reseal 46 typically functions to permit the insertion of a hollow needle or spike to establish communication with the liquid in the tube 42 while the reseal seals tightly around the periphery of the needle. The needle can be later withdrawn, and the reseal 46, owing to the inherent resiliency of the reseal material, closes at the penetration site from which the needle has been removed so as to prevent egress of the liquid.

When a toxic drug is provided in a vial 12 for being admixed with a diluent liquid in a bag 20 as described above, the vial 12 and bag 20 are typically manipulated in a controlled environment, such as in a laminar flow hood (not illustrated). The hood is maintained under negative pressure to prevent the escape of toxic vapors if there should be any inadvertent leak and to otherwise provide protection to the person handling the components. Although conventional vials and bags are typically manufactured under strict quality control standards and function well to prevent inadvertent leakage when properly handled, there is a desire, because of the highly toxic nature of many of the drugs, to provide an improved system for eliminating or reducing the likelihood that personnel will be exposed to the drugs during the reconstitution process and thereafter when the reconstituted drug is stored and used.

Figure 4:
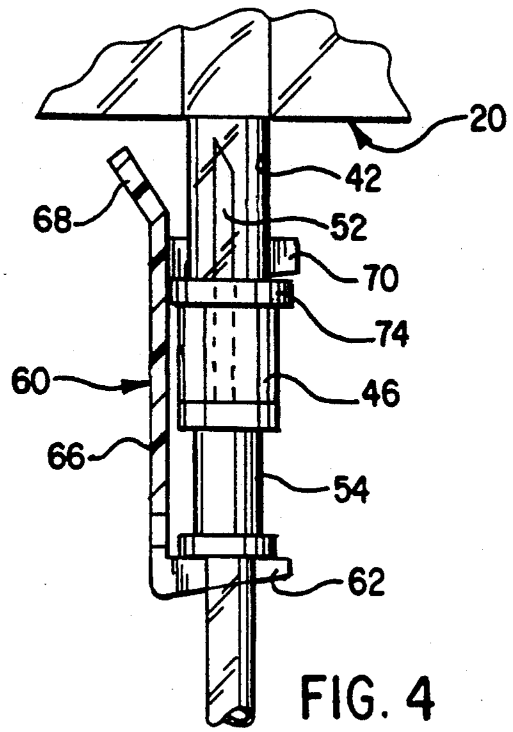
FIG. 4 is an enlarged, fragmentary, side elevational view taken generally along the plane 4—4 in FIG. 2.

To this end, one aspect of the present invention provides a novel protection system for use with a container of hazardous liquid, including the above-described pouch 20 and connected vial 12. In the preferred form of the protection system illustrated in FIG. 1, a first connecting means 50 is provided for being connected to the container 20 to establish fluid communication between the exterior of the container 20 and the liquid inside the container. In the preferred form illustrated, the connecting means 50 includes a hollow, sharp spike 52 which is mounted to one end of a hollow, cylindrical fitment 54 (FIGS. 1 and 4). The other end of the fitment 54 is sealed to a hollow, flexible tube or other suitable conduit 56 in a manner that establishes fluid communication between the interior of the hollow spike 52 and the conduit 56. The attachment of the hollow spike 52 to the conduit 56 via the fitment 54 may employ conventional, interior, sealing and mounting configurations (not visible in the FIGURES) well known to those of ordinary skill in the art. The detailed design and specific structure of such a connection, and the detailed design and specific structure of the hollow spike 52, form no part of the present invention.

A latch or clip 60 (FIGS. 1 and 4) is provided to hold the spike 52 to the container 20. The clip 60 has a pair of feet 62 at one end which are mounted to the conduit 56 adjacent the fitment 54. A spring arm 66 extends from the feet 62 and terminates in a tab 68. A pair of latch bars 70 extend outwardly from the spring arm 66 for frictionally engaging one side of a flange 74 on the conduit 42.

Initially, the clip 60 is held outwardly (as shown in FIG. 1) while the hollow spike 52 is forced into the reseal 46. Then the clip 60 is then pushed toward the tube 42 so that the arms 70 engage the flange 74 and prevent inadvertent withdrawal of the hollow spike 52.

Typically, the vial 12 and bag 20 would be screwed together before the hollow spike 52 is inserted through the reseal 46. However, the hollow spike 52 could be inserted through the reseal 46 first, and the vial 12 and bag 20 could be subsequently connected together.

A unique, flexible barrier 80 (FIGS. 1 and 2) is provided as an integral part of the system along with the conduit 56 and connecting means 50. The flexible barrier 80 is penetrated by the conduit 56 and is sealed about the periphery of the conduit 56 at the penetration.

The barrier 80 is preferably fabricated from a suitable material which is sufficiently transparent to permit some degree of visual inspection through the barrier. The barrier 80 preferably is fabricated from a synthetic, thermoplastic, polymer material, and preferably has the shape of an open-ended enclosure, bag, pouch, envelope, or the like. A preferred material for the barrier 80 is linear low density polyethylene or flexible polyvinyl chloride.

The barrier 80 is sufficiently flexible to accommodate an initial arrangement in a retracted orientation (FIG. 1) which permits access to, and manipulation of, at least a portion of the connecting means 50 and a container, such as the container 20. The barrier 80 is also sufficiently flexible to accommodate a subsequent arrangement in an extended orientation (FIG. 2) for defining an enclosure around the connecting means 50 and connected container 20.

Figure 3:
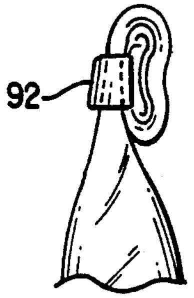
FIG. 3 is an enlarged, fragmentary, side-elevational view taken generally along the plane 3—3 in FIG. 2.

The open end of the barrier 80 is preferably provided with a sealing means for completely closing or sealing the open end of the barrier 80. To this end, one such sealing means is illustrated in FIGS. 1–3 and includes a pliable, but non-resilient, member carried in the wall of the barrier 80 and having end portions 92 projecting from the wall of the barrier 80. After the barrier 80 has been arranged to enclose the vial 12 and bag 20 as illustrated in FIG. 2, the open end of the barrier 80 can be closed and then folded over a few times (as illustrated in FIGS. 2 and 3). The extending ends 92 of the pliable member can then be bent around each side of the unfolded portion of the barrier to hold the folds tightly against the unfolded portion of the barrier. This effects a generally leak-tight seal. Other forms of closures or seals for the open end of the barrier 80 may be employed, and such other forms may be of a suitable special or conventional design.

The conduit 56 may be characterized as generally extending from the first connecting means 50, through the barrier 80, and to a discharge location exterior of, and spaced-away from, the bag 20. The conduit 56 includes a one-way, non-return valve or check valve 102. The check valve 102 prevents flow into the container or bag 20.

The check valve 102 may be of a suitable special or conventional design. A suitable conventional valve is that sold in the U.S.A. under the designation Normally Closed Check Valve by Burron Medical having an office at Bethlehem, Pennsylvania.

In the preferred embodiment illustrated in FIGS. 1 and 2, a special or conventional Y-fitment or fitting 108 is provided in the first conduit 56 for reasons described in detail hereinafter. The Y-fitting 108 is connected to the conduit 56 between an inlet leg of the "Y" and the common outlet leg of the "Y".

The Y-fitting 108 may be of a suitable special or conventional design. One suitable conventional Y-fitting is made under the designation List No. 75-0128 Y-fitment by Abbott Laboratories having an office at North Chicago, Illinois.

A second connecting means 116 is connected to the distal end of the first conduit 56, and the second connecting means 116 is adapted to be connected to a syringe 120 to establish fluid communication between the bag 20 and the syringe 120. The second connecting means 116 may be a special or conventional device, and one such suitable device is a valve sold in the U.S.A. under the designation "Burron Reflux" by Burron Medical which has an office at Bethlehem, Pennsylvania.

Such a valve has an internal valve member (not visible) that is normally biased to occlude a discharge port, and the discharge port includes a generally cylindrical receiving wall around the port for accommodating the insertion of the distal end of the syringe 120.

In a preferred form illustrated in FIG. 1, the second connecting means 116, in the form of the above-described valve, defines a conventional, female, luer fitment for receiving a mating, male, luer fitment on the distal end of the syringe 120. When the male luer fitment of the syringe 120 is inserted into the female luer fitment of the valve, the valve member within the valve is pushed away from its seat by an internal cage engage with the distal end of the syringe luer fitment. This opens the valve port and permits the liquid to be discharged through, or drawn through, the valve by operation of the syringe 120 in the usual manner to effect a suction within the syringe 120.

When the desired amount of liquid has been drawn into the syringe 120, the syringe is pulled out of the valve (i.e., connecting means 116), and the internal valve member is biased to again occlude, and seal, the valve port.

A suitable safety cap 126 may be provided for being mounted on the distal end of the valve or connecting means 116. To this end, the cap 126 may be of the conventional type normally provided with such a valve wherein the cap 126 includes a suitable internal thread structure for engaging a mating thread form or partial thread form on the exterior of the distal end of the valve.

In the preferred form of the invention illustrated in FIGS. 1 and 2, a second conduit or tube 132 is connected at a first end to the second leg of the Y fitting 108 in fluid communication with the first conduit 56. The second conduit 132 extends back through the barrier 80 to a receptacle 140. In the preferred form illustrated in FIGS. 1 and 2, the receptacle 140 has the form of a flexible pouch or bag defined by two sheets of flexible material with generally coterminous edges which are sealed together about their peripheries. The interior of the receptacle or pouch 140 is in fluid communication with the interior of the second conduit 132.

At the location where the second conduit 132 penetrates the barrier 80, the barrier 80 is sealed around the periphery of the second conduit 132 by suitable special or conventional means such as described above with respect to the barrier penetration seal for the first conduit 56.

The second conduit 132 includes a second, one-way, non-return valve 150 for preventing flow of liquid from the receptacle or pouch 140 into the first conduit 56. The one-way, non-return valve 150 may be a special or conventional check valve identical to the valve 102 employed in the first conduit 56 as described above. However, the second check valve 150 is, of course, oriented in the direction opposite to that of the orientation of the first check valve 102 so that the second check valve 150 prevents flow toward the Y-fitting whereas the first check valve 102 prevents flow away from the Y-fitting 108.

Figure 5:
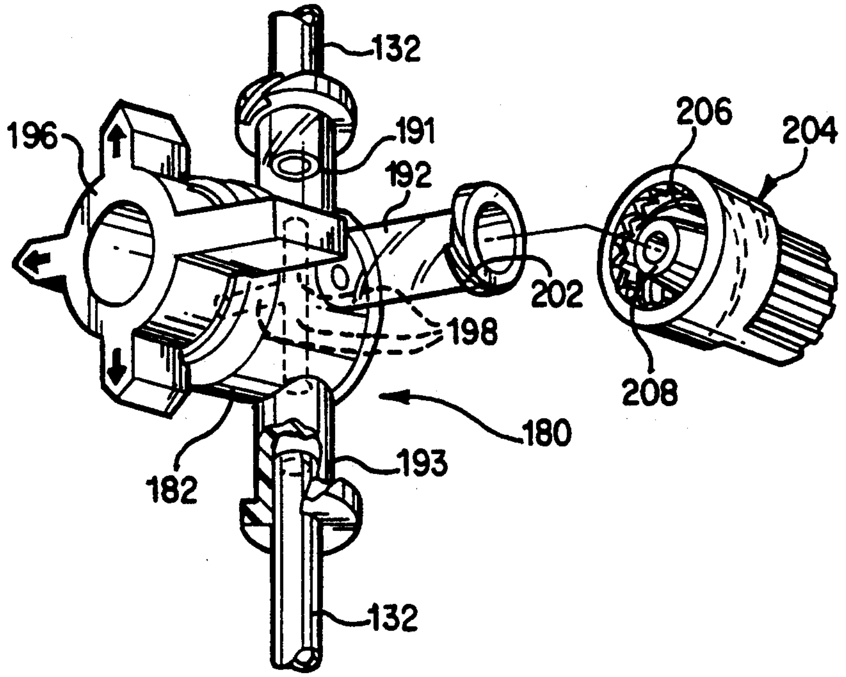
FIG. 5 is an enlarged, fragmentary, elevational view taken generally along the plane 5—5 in FIG. 2.

The preferred form of the invention illustrated in FIGS. 1 and 2 also includes a three-way valve 180 which, as illustrated in FIGS. 1 and 2, is located in the second conduit 132 between the receptacle 140 and the second check valve 150. As illustrated in FIG. 5, the three-way valve 180 includes a body 182 with three outwardly projecting conduit members 191, 192, and 193 which each define a port communicating with the interior of the valve body 182.

The valve 180 also includes a rotatable valve member 196 defining an internal, T-shaped flow passage 198. Rotation of the valve member 196 permits the internal flow passage 198 in the valve member 196 to be aligned between the port conduits 191 and 193 while occluding the port conduit 192 as illustrated in FIG. 5. The valve member 196 can also be rotated to another position to establish fluid communication between the port conduits 192 and 193 while occluding the port conduit 191. Of course, the two other positions of the valve member 196 are possible, but such other positions would not typically be employed during the use of the invention, and such other positions are not described in detail herein.

At least the port conduit 192 may be provided with an exterior thread form 202 for receiving a safety cap 204. The safety cap 204 includes an internal thread form 206 for matingly engaging the thread form 202 on the port conduit 192 and also includes an internal, hollow, cylindrical plug member 208 for being received within, and occluding, the port 192.

The valve 180 may be a conventional valve such as the valve sold under the designation 4 Way Stopcock by Medex, Inc. having an office at Hilliard, Ohio.

In operation, when the connecting means 50 is connected to the bag 20 and the barrier 80 is closed around the bag 20 as described above with reference to FIG. 2, the receptacle 140 is disposed generally adjacent the bag 20 and is also necessarily enveloped and enclosed by the barrier 80.

A leak-tight barrier or protection system is established when the top of the barrier 80 is folded together and rolled down a few turns and secured in position by the pliable tabs 92 as described above and illustrated in FIGS. 2 and 3. With the leak-tightness of the barrier system thus established, the plug 34 can be removed from the lower end of the neck 26 of the bag 20 to permit the contents of the vial 12 to be discharged into the bag 20 and be mixed therein.

When the barrier 80 is in the fully sealed orientation as illustrated in FIG. 2, the discharge valve 116 and the three-way valve 180 are, of course, exposed for manipulation. The syringe 120 can be engaged with the distal end of the discharge valve 116, and a desired amount of liquid can be withdrawn from the bag 20 by operation of the syringe to establish suction within the syringe.

If an air bubble is entrained with the liquid flowing into the syringe, or if excess liquid is drawn into the syringe, the air bubble and/or excess liquid can be discharged into the receptacle 140. To this end, the syringe 120 is operated to discharge the desired amount of the liquid back through the valve 116. The check valve 102 in the first conduit 56 prevents back flow into the bulk supply bag 20, but the check valve 150 permits flow from the syringe 120 toward the receptacle 140. If the valve member 196 of the three-way valve 180 is aligned as illustrated in FIG. 5, the liquid discharged from the syringe 120 can pass into the receptacle 140 within the barrier 180. In this manner, a small amount of liquid containing an entrained air bubble or a small amount of excess liquid can be conveniently discharged to the receptacle 140 without requiring removal of the syringe 120 from the valve 116.

Thus, the receptacle 140 functions as a waste receptacle within the barrier 80. Further, because the receptacle 140 is separate from the bulk supply bag 20, and because the check valve 102 does not permit flow back into the bag 20, there is no danger that the bulk supply in the bag 20 can become contaminated with the liquid that had been previously withdrawn from the bag 20.

If desired, the system may be operated in a "pumping" mode so as to pump liquid from the bulk supply bag 20 to a separate container or remote location. Specifically, the valve member 196 in the three-way valve 180 can be oriented to establish communication between the second conduit 132 and the outlet port conduit 192 while occluding the port conduit 191. The outlet port conduit 192 can be connected directly to a separate fluid conduit system or to a separate container, such as to a container of an intravenous fluid. The syringe 120 can be operated to first withdraw liquid from the bag 20 into the syringe, and then the syringe can be operated to force the liquid from the syringe through the conduit 132 and three-way valve 180 to the other container or fluid conduit system (not illustrated).

The first connecting means 50 has been illustrated as incorporating a hollow spike 52 for use with a suitable reseal 46, and the second connecting means 116 has been illustrated as a valve for use with a suitable syringe 120. It will be appreciated, however, that other systems may be provided for establishing a connection with the bulk supply bag 20 and for effecting a dispensing of the liquid from the end of the conduit 56. Thus, the first connecting means 50, the conduit 56, and the second connecting means 116 (which could be a dispensing valve as previously described), may be characterized together in general terms as a first conduit system or means for being connected to, and extending from, the container 20 to define a flow path for the liquid from the container to a discharge location exterior of the container 20. Similarly, the second conduit 132 may be characterized as a second conduit means for defining a flow path for the liquid between a first end connected in fluid communication with the first conduit means and a second end connected to the receptacle 140.

Further, it will be appreciated that although one aspect of the present invention relates to the use of the novel barrier 80 with both a first conduit means for withdrawing a liquid and a second conduit means connected to a receptacle for accommodating excess or waste liquid, the second conduit means 132 and connected receptacle 140 may be omitted, or at least not used, in those situations where there is no need to hold excess liquid in a separate, sealed receptacle.

Further, there may be applications involving liquids which are not directly hazardous to personnel but which may be potentially damaging to the environment if not disposed of in an appropriate manner. In other applications, a liquid may not be directly hazardous and may not even pose a potential danger to the environment, but may be subject to strict inventory control. Thus, another aspect of the present invention contemplates that in either of these situations the system may be provided without the barrier 80. Without the barrier 80, the system would still conveniently accommodate the collection of the waste or excess liquid in the receptacle 140 so that the liquid in the receptacle 140 would be readily susceptible to inventory control processing and/or proper disposal.

Figure 6:
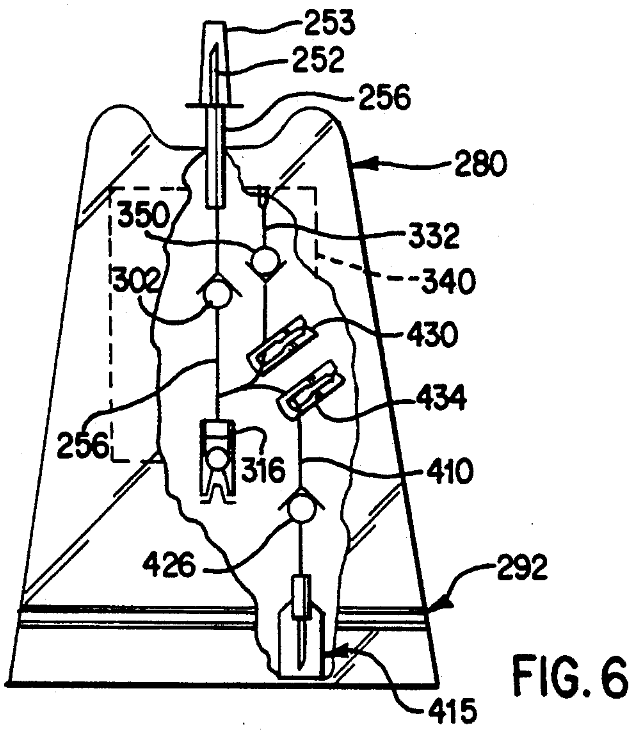
FIG. 6 is a simplified, diagrammatic, front elevation view of a second embodiment of the invention wherein the components are shown in a first arrangement prior to use.

A second embodiment of the present invention is diagrammatically illustrated in FIG. 6. This embodiment includes a barrier protection system in combination with a liquid transfer system that incorporates means for transferring liquid to a syringe, to another fluid conducting system or container, and to a waste receptacle.

Figure 7:
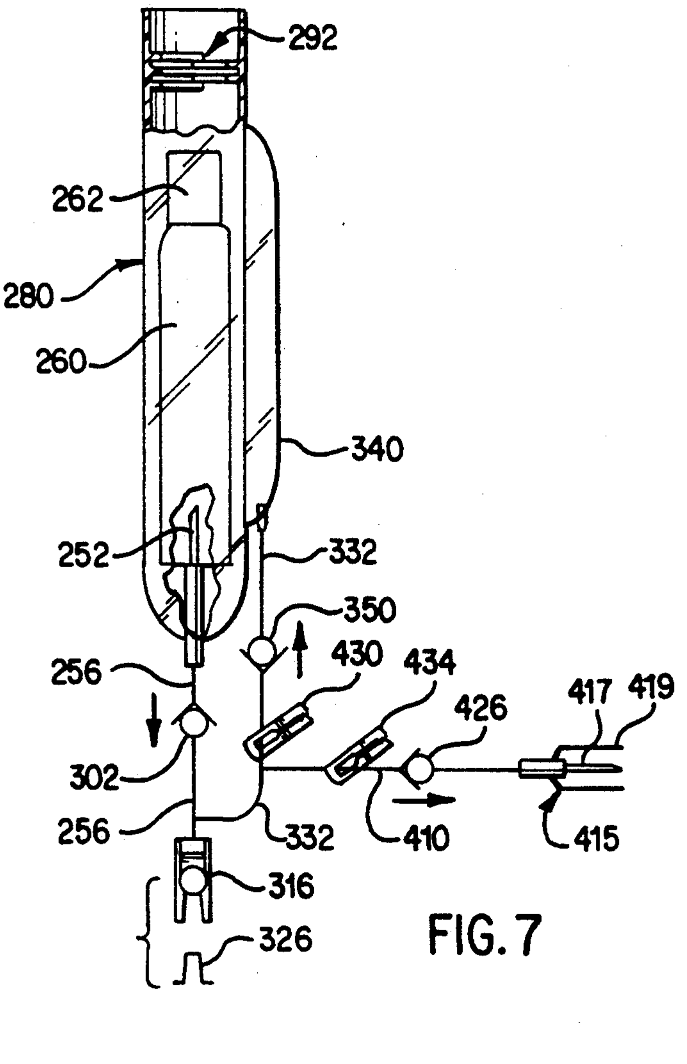
FIG. 7 is a simplified, diagrammatic view similar to FIG. 6, but showing a side elevation after the components have been connected to a bag containing a bulk reconstituted supply of an admixed drug from an attached vial and wherein the system components are in a second arrangement providing an enveloping barrier against leakage.

The second embodiment includes a first connecting means, such as a hollow spike 252. The spike 252 is adapted to penetrate a closure member, such as a reseal (not illustrated), in a bulk supply bag or container 260 (FIG. 7). Such a reseal and container may be substantially the same as the reseal 46 and associated container 20 described above with reference to the first embodiment of the invention illustrated in FIGS. 1-5. In FIG. 7, the reseal or other closure contained on or in the container 260 has been omitted for ease of illustration, and the hollow spike 252 is shown penetrating the bottom of the container 260.

Prior to use, the hollow spike 252 may be covered with a suitable safety cap 253. The spike 252 is mounted on the end of a first conduit 256 which penetrates a barrier 280. The barrier 280 is flexible, and may be fabricated from the same material as the barrier 80 described above with reference to the first embodiment illustrated in FIGS. 1-5. The barrier 280 is sealed around the periphery of the first conduit 256 at the location where the first conduit 256 penetrates the barrier. The barrier 280 has a configuration that permits its arrangement in an initial, retracted orientation which permits access to, and manipulation of, the connecting means spike 252 and container 260. Such an initial orientation is illustrated in FIG. 6.

The bag 280 accommodates subsequent arrangement in an extended orientation (FIG. 7) for defining an enclosure around the first connecting means 252 and container 260. The top of the container 260 may be adapted to be coupled to another container 262. The container 262 may be substantially identical to the vial 12 described above with reference to the first embodiment illustrated in FIGS. 1 and 2. Thus, the contents from the container 262 can be emptied into, and mixed with, a diluent or other liquid contained in the container 260. Of course, the assembly of the container 260 coupled to the container 262 may not be the only means for supplying liquid to the hollow spike 252. Other containers could be used, including a single container of a premixed, bulk supply of liquid.

In any event, the barrier 280 is adapted to be sealed at its open end by suitable means. FIG. 7 illustrates the use of a interlocking, plastic rib zipper-type seal 292 which may be of a suitable special or conventional design, the details of which form no part of the present invention.

The barrier 280 preferably has a wedge-shaped, open-ended, envelope configuration which is substantially reversible from the inside-out orientation illustrated in FIG. 6 to the inverted orientation illustrated in FIG. 7. As schematically represented in FIG. 7, a first one-way, non-return valve or check valve 302 is mounted in the first conduit or tube 256 to prevent flow back into the bag 280. The check valve 302 may be a suitable special or conventional check valve and may be identical to the check valve 102 described above with reference to the first embodiment of the invention illustrated in FIGS. 1-5.

A second connecting means or dispensing valve 316, which includes a removable safety cap 326, is mounted to the distal end of the first conduit 256. The valve 316 may be a suitable special or conventional valve adapted for use with a syringe (not illustrated) and may be identical to the valve employed as the second connecting means 116 described above with reference to the embodiment illustrated in FIGS. 1-5.

A second conduit means or tube 332 extends from the first conduit 256 to a receptacle 340. The receptacle 340 includes a sheet of flexible, thermoplastic material sealed about its periphery to the outside surface of the barrier 280. The receptacle 340 functions in the same manner as the receptacle 140 in the first embodiment described above with reference to FIGS. 1-5, and the receptacle 340 receives excess or waste liquid and/or entrained air.

A one-way, non-return valve or check valve 350 is provided in the second conduit 332 as schematically illustrated in FIG. 7. The check valve 350 prevents flow out of the receptacle 340. The check valve 350 may be a suitable special or conventional valve and may be identical to the check valve 150 described above with reference to the first embodiment of the invention illustrated in FIGS. 1-5.

A third conduit 410 is connected at one end in fluid communication with the second conduit 332 between the first conduit 256 and the second check valve 350. The third conduit 410 terminates in a second end having a suitable dispensing structure or fitment 415 from which liquid may be discharged. The fitment 415, as schematically illustrated in FIG. 7, may be a conventional connection of the kind sold under the designation LIFE-SHIELD TM Connector in the U.S.A. by Abbott Laboratories having an office at North Chicago, Illinois. Such a fitment 415 includes a hollow spike 417 surrounded by a cylindrical shield 419. The fitment 415 is adapted to be connected to a suitable receiving port in an intravenous bag system (not illustrated). The detailed design and structure of the fitment 415 form no part of the present invention.

In order to prevent flow from the third conduit 410 back into the second conduit 332, a third one-way, non-return valve or check valve 426 is provided in the third conduit 410. The check valve 426 may be identical to the check valve 350 described above.

In the embodiment illustrated in FIG. 7, there is no three-way valve, such as the three-way valve 180 illustrated in FIG. 5 for the previously described first embodiment. Rather, a conventional slide clamp 430 is provided on the second conduit 332, and a second slide clamp 434 is provided on the third conduit 410. The slide clamps 430 and 434 may have a suitable special or conventional design. A suitable conventional clamp is made under the designation List No. 75-0187 Slide Clamp by Abbott Laboratories having an office at North Chicago, Illinois. Each slide clamp functions as an isolation valve means for selectively closing or opening the conduit on which it is mounted.

The two slide clamps 430 and 434 can be employed to selectively direct the flow to either the receptacle 340 or the fitment 415. In particular, if it is desired to discharge excess or waste liquid, including liquid with entrained air, to the receptacle 340, then the slide clamp 434 is adjusted to close off the conduit 410, and the clamp 430 is maintained in an open position on the second conduit 332. Alternatively, if it is desired to transfer liquid to the third conduit 410, the slide clamp 434 is adjusted to the open position, and then the slide clamp 430 is adjusted to the closed position so as to pinch the second conduit 332 closed.

With the system illustrated in FIG. 7, a syringe, such as the syringe 120 described above with reference to the first embodiment illustrated in FIGS. 1-5, may be employed for withdrawing liquid from the container 260. Further, liquid can be "pumped" from the container 260 through the third conduit 410 by operation of the syringe in the same manner as described above with reference to the first embodiment.

The barrier system of the invention functions to protect personnel from a hazardous liquid leak, and the barrier system can be relatively easily and quickly manipulated as necessary to provide the barrier protection around a variety of containers having various shapes and sizes.

Further, regardless of whether or not the barrier protection system is needed or employed, an additional feature of the invention provides a novel liquid transfer system for accommodating withdrawal of liquid from a container with a syringe. The system permits the syringe to be used as a pump to discharge precise amounts of the liquid directly to another fluid conduit system or to an intravenous container—all without opening the system to ambient atmosphere.

It will be readily apparent from the foregoing detailed description of the invention and from the illustrations thereof that numerous variations and modifications may be effected without departing from the true spirit and scope of the novel concepts or principles of this invention.

What is claimed is:

1. A protection system adopted for use with a container from which a hazardous liquid can be removed, said system comprising:

conduit means for being connected to, and extending from, said container to define a flow path for said liquid from said container to a discharge location exterior of the container; and a flexible barrier that is impervious to said liquid and that is penetrated by, and sealed to, said conduit means for accommodating (1) an initial arrangement in a retracted orientation permitting access to, and manipulation of, at least a portion of said conduit means and container, and (2) a subsequent arrangement, in an extended orientation enveloping said portion of said conduit means and the connected container.

2. The protection system in accordance with claim 1 said conduit means includes a first connecting means for being connected to said container, a first conduit extending from said first connecting means, and a second connecting means on the said first conduit for being connected to a syringe.

3. The protection system in accordance with claim 1 in which said flexible barrier comprises thermoplastic material having a generally tubular configuration that is closed at one end sealed about said conduit means and that is open at the other end.

4. The protection system in accordance with claim 3 further including a releasable sealing means at the open end of said tubular configuration for sealing closed the open end.

5. The protection system in accordance with claim 1 in which said conduit means includes a first conduit;

said system further includes a second conduit connected at one end to said first conduit; and said system further includes a receptacle connected to said second conduit in fluid communication therewith.

6. The protection system in accordance with claim 1 further including a receptacle in fluid communication with said conduit means, said receptacle being integral with said conduit means and flexible barrier.

7. The protection system in accordance with claim 6 in which said flexible barrier comprises thermoplastic film having a generally tubular configuration and said receptacle is carried on an exterior surface of the tubular configuration when said barrier is arranged in said extended orientation enveloping said portion of said conduit means and the connected container.

8. The protection system in accordance with claim 6 in which said receptacle is disposed relative to said barrier for being located within, and enclosed by, said barrier when said barrier is arranged in said extended orientation enveloping said portion of said conduit means and the connected container.

9. The protection system in accordance with claim 1 in which said conduit means includes a connecting means for being connected to said container, a flexible conduit connected to said connecting means, and a distal end terminating in a discharge location exterior of the container; and said system further includes a one-way, non-return valve in said flexible conduit to prevent flow of liquid back into said container.

10. A protection system adopted for use with a container from which a hazardous liquid can be removed, said system comprising:

connecting means for being connected to said container to establish fluid communication between the exterior of the container and the liquid inside the container;

a conduit extending from said connecting means to define a flow path for said liquid from said connecting means to a discharge location exterior of the container; and a flexible barrier penetrated by said conduit, said barrier being sealed about the periphery of said conduit at the penetration and being impervious to said liquid, said barrier accommodating an initial arrangement in a retracted orientation permitting access to, and manipulation of, at least a portion of said connecting means and container, and said barrier accommodating a subsequent arrangement in an extended orientation for defining an enclosure around said portion of said connecting means and the connected container.

11. The protection system in accordance with claim 10 in which said connecting means includes a hollow spike adapted to penetrate a seal on said container and includes a clip for holding said hollow spike and container together.

12. The protection system in accordance with claim 10 further including a discharge valve on the distal end of said conduit for accommodating connection to a syringe.

* * * * *